United States Patent
Dahlin et al.

(10) Patent No.: US 12,173,276 B2
(45) Date of Patent: Dec. 24, 2024

(54) **HETEROLOGOUS EXPRESSION OF PHOSPHITE DEHYDROGENASE IN *PICOCHLORUM* SPP**

(71) Applicant: Alliance for Sustainable Energy, LLC, Golden, CO (US)

(72) Inventors: Lukas Royce Dahlin, Golden, CO (US); Michael T. Guarnieri, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 17/951,848

(22) Filed: Sep. 23, 2022

(65) Prior Publication Data

US 2023/0110210 A1    Apr. 13, 2023

Related U.S. Application Data

(60) Provisional application No. 63/248,213, filed on Sep. 24, 2021.

(51) Int. Cl.
*C12N 1/12* (2006.01)
*C12N 9/02* (2006.01)
*C12N 15/82* (2006.01)

(52) U.S. Cl.
CPC .............. *C12N 1/12* (2013.01); *C12N 9/0004* (2013.01); *C12N 15/8214* (2013.01); *C12N 15/8243* (2013.01); *C12Y 120/01001* (2013.01); *C12N 2800/10* (2013.01)

(58) Field of Classification Search
CPC ........................................................ C12N 1/12
See application file for complete search history.

(56) References Cited

PUBLICATIONS

Cutolo, et al., Algal Research 59 (2021) 102429, pp. 1-9 (Year: 2021).*
Dahlin, et al., Communications Biology | (2019) 2:388, pp. 1-10 (Year: 2019).*
Krishnan, et al., Algal Research, 2020. 101944, pp. 1-7 (Year: 2020).*
Changko, et al., Applied Microbiology and Biotechnology (2020) 104:675-686 (Year: 2020).*
Lanza, et al. BMC Systems Biology 2014, 8:33, pp. 1-10 (Year: 2014).*
Hirota, et al., Scientific Reports, 2017, 7:44748, pp. 1-10 (Year: 2017).*
Loera-Quezada, et al., Plant Biotechnology Journal (2016) 14, pp. 2066-2076 (Year: 2016).*
Changko et al., "The phosphite oxidoreductase gene, ptxD as a bio-contained chloroplast marker and crop-protection tool for algal biotechnology using *Chlamydomonas*" Applied Microbiology and Biotechnology, 2020, vol. 104, pp. 675-686.
Dahlin et al., "Heterologous expression of phosphite dehydrogenase in the chloroplast or nucleus enables phosphite utilization and genetic selection in *Picochlorum* spp.", Algal Research, Mar. 2022, vol. 62, No. 102604, pp. 1-6.
López-Arredondo et al., "Engineering phosphorus metabolism in plants to produce a dual fertilization and weed control system", Nature Biotechnology, Sep. 2012, vol. 30, No. 9, pp. 889-893.
Pandeya et al., "Selective fertilization with phosphite allows unhindered growth of cotton plants expressing the ptxD gene while suppressing weeds", PNAS, 2018, vol. 115, No. 29, pages E6946-E6955.
Sandoval-Vargas et al., "Chloroplast engineering of *Chlamydomonas reinhardtii* to use phosphite as phosphorus source", Algal Research, Jul. 2018, vol. 33, pp. 291-297.
Sandoval-Vargas et al., "Use of the ptxD gene as a portable selectable marker for chloroplast transformation in *Chlamydomonas reinhardtii*", Molecular Biotechnology, 2019, vol. 61, pp. 461-468.

* cited by examiner

*Primary Examiner* — Louise W Humphrey
*Assistant Examiner* — Jessica Faye Edwards
(74) *Attorney, Agent, or Firm* — Sam J. Barkley

(57) ABSTRACT

Phosphite dehydrogenase (ptxD) expression was established as a selectable marker for nuclear and chloroplast genetic selection in Picochlorum renovo and Picochlorum celeri Phosphite was used as a sole phosphorus source in P. renovo and P. celeri. Growth on phosphite led to comparable growth and composition relative to phosphate.

18 Claims, 6 Drawing Sheets

Specification includes a Sequence Listing.

A

B

SEQUENCE LISTING

```
Sequence total quantity: 4
SEQ ID NO: 1           moltype = DNA   length = 1011
FEATURE                Location/Qualifiers
source                 1..1011
                       mol_type = other DNA
                       organism = synthetic construct
SEQUENCE: 1
atgttaccta aattagttat tacacatcgt gtacatgatg aaatacttca attacttgca   60
ccacattgtg aattaatgac aaatcaaact gattcaacat taacacgtga agaaatttta  120
cgacgctgtc gtgatgctca agctatgatg gcatttatgc cagatcgtgt tgatgcagat  180
ttttacaag catgtccaga attacgtgtt gttggttgtg ctttaaaagg ttttgataat  240
tttgatgtta atgcatgtac agctcgtggt gtttggttaa catttgttcc tgatttatta  300
actgtaccaa cagcagaact agcaattggt ttagcggttg gattaggtcg tcatttacgt  360
```

```
gcagcggatg cttttgtacg ttcaggtgaa tttcaaggtt ggcaaccaca attttatggt  420
acaggtttag ataatgcaac agtaggtatt ttaggtatgg gtgctattgg tttagcaatg  480
gctgatcgat tacaaggttg gggtgcaact ttacaatatc atgctcgtaa agcattagat  540
acacaaacag aacaacgttt aggacttcgt caagttgctt gttcagaatt atttgcttca  600
tcagatttta ttttattagc tttaccatta aatgctgata ctcaacattt agttaatgct  660
gaattattag cacttgttcg accaggtgcg ctattagtaa atccttgtcg tggtagtgtt  720
gtagatgaag ctgctgtttt agctgcatta gaacgaggtc aacttggtgg ttatgcagct  780
gatgtatttg aaatggaaga ttgggctcga gcagatcgtc cacgtttaat tgatccagca  840
ttattagcac atccaaatac attattaca ccacatattg gatcagcagt tcgtgctgta  900
cgcttagaaa ttgaacgttg tgcagcacaa aatattattc aagtattagc tggtgcacgt  960
ccaattaatg cagcaaatcg tttaccaaaa gctgaaccag ctgcttgtta a          1011

SEQ ID NO: 2              moltype = AA  length = 336
FEATURE                   Location/Qualifiers
source                    1..336
                          mol_type = protein
                          organism = synthetic construct
SEQUENCE: 2
MLPKLVITHR VHDEILQLLA PHCELMTNQT DSTLTREEIL RRCRDAQAMM AFMPDRVDAD   60
FLQACPELRV VGCALKGFDN FDVDACTARG VWLTFVPDLL TVPTAELAIG LAVGLGRHLR  120
AADAFVRSGE FQGWQPQFYG TGLDNATVGI LGMGAIGLAM ADRLQGWGAT LQYHARKALD  180
TQTEQRLGLR QVACSELFAS SDFILLALPL NADTQHLVNA ELLALVRPGA LLVNPCRGSV  240
VDEAAVLAAL ERGQLGGYAA DVFEMEDWAR ADRPRLIDPA LLAHPNTLFT PHIGSAVRAV  300
RLEIERCAAQ NIIQVLAGAR PINAANRLPK AEPAAC                            336

SEQ ID NO: 3              moltype = DNA  length = 1011
FEATURE                   Location/Qualifiers
source                    1..1011
                          mol_type = other DNA
                          organism = synthetic construct
SEQUENCE: 3
atgttgccaa aactggttat aactcatcgt gttcacgacg aaattctcca gttgctcgcc   60
ccacattgtg aacttatgac gaaccagacc gatagtacgc tcacaagaga agagattttg  120
agacgatgca gggacgctca agcgatgatg ctttcatgc ccgatagagt ggatgccgat  180
ttcttgcagg cttgcccaga gctgcgcgtt gtcggatgcg cgcttaaggg gttcgacaat  240
ttcgatgttg atgcatgtac agcgagaggt gtgtggttga cctttgtccc ggatctcttg  300
accgtcccca cagcggaact cgctatcggg ttggccgtgg gattggggag gcacctgcgc  360
gctgcagatg cttttgtacg ctcaggtgaa tttcagggt ggcagccaca attttacggg  420
acaggacttg ataacgcaac ggtgggatt cttgggatgg gagctatcgg tttggctatg  480
gcagatagac tccagggttg gggggcaact ctccaatatc acgaggctaa ggctctggat  540
acccaaacag agcagcgctt gggattgcgt caggtcgcct gcagtgagct ttttgcatct  600
tccgatttca tccttttggc gttgccactc aatgcagaca cacagcattt ggtgaacgca  660
gagctcttgg cactcgtgag accagggcc tgctcgtga atccatgcag agggtcggta  720
gtcgatgagg cagcggtgct cgctgcattg gaaaggggac agcttggagg ttacgctgca  780
gacgtattcg agatggagga ttgggccaga gcagatagac ctcgcctgat cgatccagct  840
ctcttggcgc atccaaatac tctgtttaca ccccatattg gaagtgccgt gagagcggtg  900
cgtttggaaa tagaaagatg tgccgctcag aatatcattc aagtcttggc tggagctaga  960
ccaattaacg ccgcgaacag attgcctaag gccgaacctg ccgcatgtta g          1011

SEQ ID NO: 4              moltype = AA  length = 336
FEATURE                   Location/Qualifiers
source                    1..336
                          mol_type = protein
                          organism = synthetic construct
SEQUENCE: 4
MLPKLVITHR VHDEILQLLA PHCELMTNQT DSTLTREEIL RRCRDAQAMM AFMPDRVDAD   60
FLQACPELRV VGCALKGFDN FDVDACTARG VWLTFVPDLL TVPTAELAIG LAVGLGRHLR  120
AADAFVRSGE FQGWQPQFYG TGLDNATVGI LGMGAIGLAM ADRLQGWGAT LQYHEAKALD  180
TQTEQRLGLR QVACSELFAS SDFILLALPL NADTQHLVNA ELLALVRPGA LLVNPCRGSV  240
VDEAAVLAAL ERGQLGGYAA DVFEMEDWAR ADRPRLIDPA LLAHPNTLFT PHIGSAVRAV  300
RLEIERCAAQ NIIQVLAGAR PINAANRLPK AEPAAC                            336
```

HETEROLOGOUS EXPRESSION OF PHOSPHITE DEHYDROGENASE IN *PICOCHLORUM* SPP

CROSS-REFERENCE TO RELATED APPLICATIONS

This application claims priority under 35 U.S.C. § 119 to U.S. provisional patent application No. 63/248,213 filed on 24 Sep. 2021, the contents of which are hereby incorporated in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

SEQUENCE LISTING

The instant application contains a Sequence Listing which has been submitted via the Patent Center and is hereby incorporated by reference in its entirety. The XML copy as filed herewith was originally created on 14 Dec. 2022. The XML copy as filed herewith is named NREL_20-66.xml, is 7,269 bytes in size and is submitted with the instant application.

BACKGROUND

Microalgae present a path to ameliorate problems associated with climate change via capture and reduction of $CO_2$ to sustainable fuels and chemicals. Picochlorum is a genus of algae recently recognized for potential application in these regards due to its high productivity, thermotolerance, and halotolerance. Foundational genetic tools have recently been established in this genus. However, at present, genetic markers are limited, hindering genetic throughput and trait stacking approaches.

SUMMARY

In an aspect, disclosed herein is a non-naturally occurring Picochlorum spp. capable of growth on phosphite as a sole phosphorus source. In an embodiment, the Picochlorum spp. is Picochlorum renovo. In an embodiment, The Picochlorum spp. is Picochlorum celeri. In an embodiment, the Picochlorum spp. contains a mutated ptxD gene with greater than 90% sequence identity to SEQ ID NO: 1. In an embodiment, the mutated ptxD gene's expressed enzyme has a sequence that is greater than 90% sequence identity to SEQ ID NO: 2. In an embodiment, the mutated ptxD gene is expressed in the plastid. In an embodiment, the expressed enzyme is capable of NADP+ and NAD+ utilization. In an embodiment, the mutated ptxD gene has a greater than 90% sequence identity to SEQ ID NO: 3. In an embodiment, the Picochlorum spp. has a mutated ptxD gene whose expressed enzyme has a sequence that is greater than 90% sequence identity to SEQ ID NO: 4. In an embodiment, the mutated ptxD gene is expressed in the nucleus. In an embodiment, the expressed enzyme of SEQ ID NO: 4 is capable of NADP+ and NAD+ utilization.

In an aspect, disclosed herein is a non-naturally occurring Picochlorum spp. capable of growth on phosphite as a sole phosphorus source comprising a mutated ptxD gene with greater than 90% sequence identity to SEQ ID NO: 1 and wherein the expressed enzyme from the mutated ptxD gene is capable of NADP+ and NAD+ utilization and wherein the non-naturally occurring Picochlorum spp. further comprises an exogenous phosphite-specific transporter. In an embodiment, the exogenous phosphite-specific transporter is HtxBCDE. In an embodiment, the Picochlorum spp. is Picochlorum renovo. In an embodiment, the Picochlorum spp. is Picochlorum celeri. In an embodiment, the mutated ptxD gene expresses an enzyme that has a sequence that is greater than 90% sequence identity to SEQ ID NO: 2. In an embodiment, the mutated ptxD gene is expressed in the plastid.

In an aspect, disclosed herein is a non-naturally occurring Picochlorum spp. capable of growth on phosphite as a sole phosphorus source comprising a mutated ptxD gene with greater than 90% sequence identity to SEQ ID NO: 3 and wherein the expressed enzyme from the mutated ptxD gene is capable of NADP+ and NAD+ utilization and wherein the non-naturally occurring Picochlorum spp. further comprises an exogenous phosphite-specific transporter. In an embodiment, the Picochlorum spp. has a mutated ptxD gene whose expressed enzyme has a sequence that is greater than 90% sequence identity to SEQ ID NO: 4. In an embodiment, the mutated ptxD gene is expressed in the nucleus.

Other objects, advantages, and novel features of the present invention will become apparent from the following detailed description of the invention when considered in conjunction with the accompanying drawings.

BRIEF DESCRIPTION OF THE DRAWINGS

FIG. 2A depicts a construct design for homologous recombination into the chloroplast genome, and random integration into the nuclear genome, right: phosphite selection agar plates, highlighting colony formation (encircled in red). FIG. 2B depicts PCR verification of transformants, primer binding is noted in panel a.

FIG. 3A depicts growth analysis of P. renovo chloroplast and nuclear transformants expressing ptxD grown on phosphite as a sole phosphorus source compared to wild-type grown on phosphate. FIGS. 3B, 3C, and 3D depict ash-free dry weight (AFDW), fatty-acid methyl esters (FAME), and carbohydrate analyses corresponding to endpoint biomass of samples in panel a. All data represents an average and standard deviation of three biological replicates.

FIG. 4A depicts gel electrophoresis showing efficacy of primer pairs used to distinguish P. renovo and P. celeri. FIG. 4B depicts a sequence alignment of relevant nuclear gDNA amplified and primer binding, forward primer binds to a protein of unknown function, reverse primer binds to the RuBisCO small subunit protein.

FIG. 5A depicts confirmation of homoplasmy for the chloroplast transformant. FIG. 5B depicts confirmation of ptxD integrated via nuclear expression elements.

FIG. 6A depicts growth analysis of P. celeri chloroplast and nuclear transformants expressing ptxD grown on phosphite as a sole phosphorus source compared to wild-type grown on phosphate. FIGS. 6B, 6C, and 6D are depicted, respectively, in the upper right, lower left, and lower right portions of FIG. 6. FIG. 6B depicts ash-free dry weight (AFDW), FIG. 6D fatty-acid methyl esters (FAME), and FIG. 6C carbohydrate analyses corresponding to endpoint biomass of samples in panel a. All data represents an average and standard deviation of four biological replicates.

DETAILED DESCRIPTION

Figure 1:
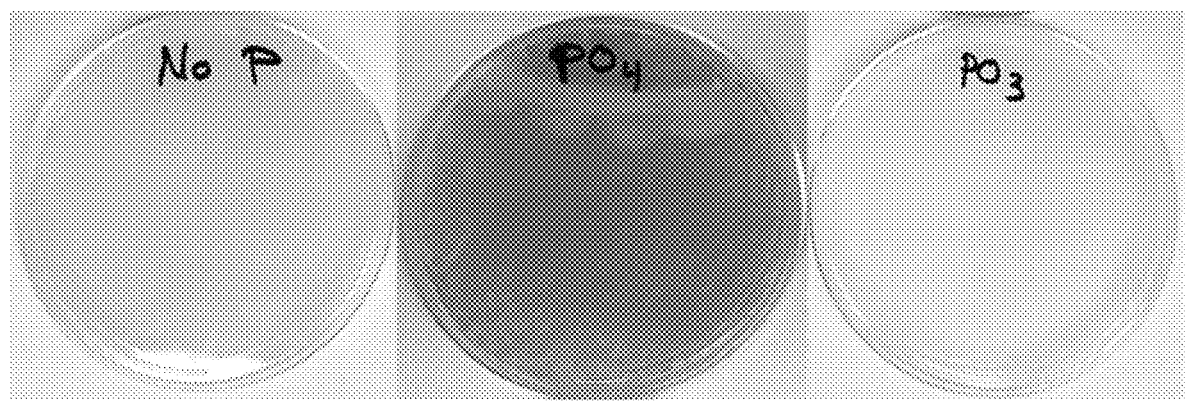
FIG. 1 depicts a plating assay to determine phosphorus source utilization capacity in P. renovo. Representative 5-day outgrowth of P. renovo with (Left to Right): no additional phosphorus source, 0.313 mM phosphate addition, and 0.313 mM phosphite addition.

Microalgae are amongst the most promising biocatalysts capable of photosynthetically converting carbon dioxide and water to renewable biomass and bioproducts. These organisms have been pursued for production of native metabolites (e.g. astaxanthin, omega-3 fatty acids), and recently for production of non-native metabolites (e.g. bisabolene) and heterologous proteins via genetic engineering, underscoring their potential impact in the emerging bioeconomy. Unlike terrestrial crops, microalgae are capable of growing in saline water and on non-arable land, while maintaining approximately an order of magnitude higher areal productivity. Despite the promise of microalgae, successful industrial application is currently limited to relatively high value products (e.g. nutraceuticals), in part due to limited genetic tractability, low productivity, and mass culture contamination events.

Development and application of genetic tools for trait stacking, targeted productivity improvements, and expansion of microalgal product suites will help to realize the benefits of microalgae as a biotechnological host for lower value commodities, such as fuel and chemical intermediates. Additionally, approaches to prevent the growth of competing algae, microbial contaminants, and predators, which can lead to low productivity and pond crashes, must be established.

Researchers have recently developed the use of phosphite, an exceedingly rare phosphorus source in nature, as a dual-pronged fertilizer and weed control system, enabled by expression of the phosphite dehydrogenase (ptxD) gene from *Pseudomonas stutzeri* WM88. The ptxD gene oxidizes phosphite to metabolically accessible phosphate, via the concurrent reduction of NAD+ to NADH. The ptxD gene can also be used as a selectable marker, via cultivation on media with phosphite as a sole phosphorus source. Since its first development in *arabidopsis* and tobacco, this technology has been further applied to rice, cotton, maize, sorghum, and yeast. Recently, phosphite mediated selection and cultivation has been applied in model algal (Chlamydomonas reinhardtii) and cyanobacterial systems, where it has proved effective for reduced contamination at up to 1000 L scale cultivation, and as a selectable marker for both nuclear and chloroplast expression. However, to date, this strategy has not been deployed in non-model algal systems with traits suitable for economically viable mass-cultivation.

Herein, we have developed phosphite utilization in the industrially relevant, emerging model algae, P. renovo and P. celeri. Algae of this genus have recently gained interest for applied biotechnology and basic science pursuits due to their rapid growth, thermotolerance, and ability to thrive at high salinities. Phosphite utilization was accomplished via expression of the ptxD gene, from either the chloroplast or nuclear genomes. Further, we demonstrate phosphite utilization as a selectable marker, broadening the genetic tools available to this genus, while also imparting potential crop protection and biocontainment traits useful for mass scale cultivation.

Phosphite Utilization Screening

P. renovo was supplemented with phosphite as the sole phosphorus source on agar plates to assess native phosphite utilization capacity and potential as a selection agent. As shown in FIG. 1, no growth was observed in the phosphite grown culture, and noticeable bleaching occurred when compared to a control with no added phosphorus source, which displayed modest growth, likely due to residual phosphorus stores (FIG. 1). Contrary to prior reports of non-toxicity in other algal systems, distinct phosphite toxicity was observed under the tested conditions. Indeed, phosphite has notable anti-fungal properties, and similar mechanisms of toxicity could be relevant in some algal systems. These results suggested that phosphite could serve as a suitable selection agent for P. renovo, using established ptxD-mediated strategies.

ptxD as a Selectable Marker

Figures 2A, 2B:
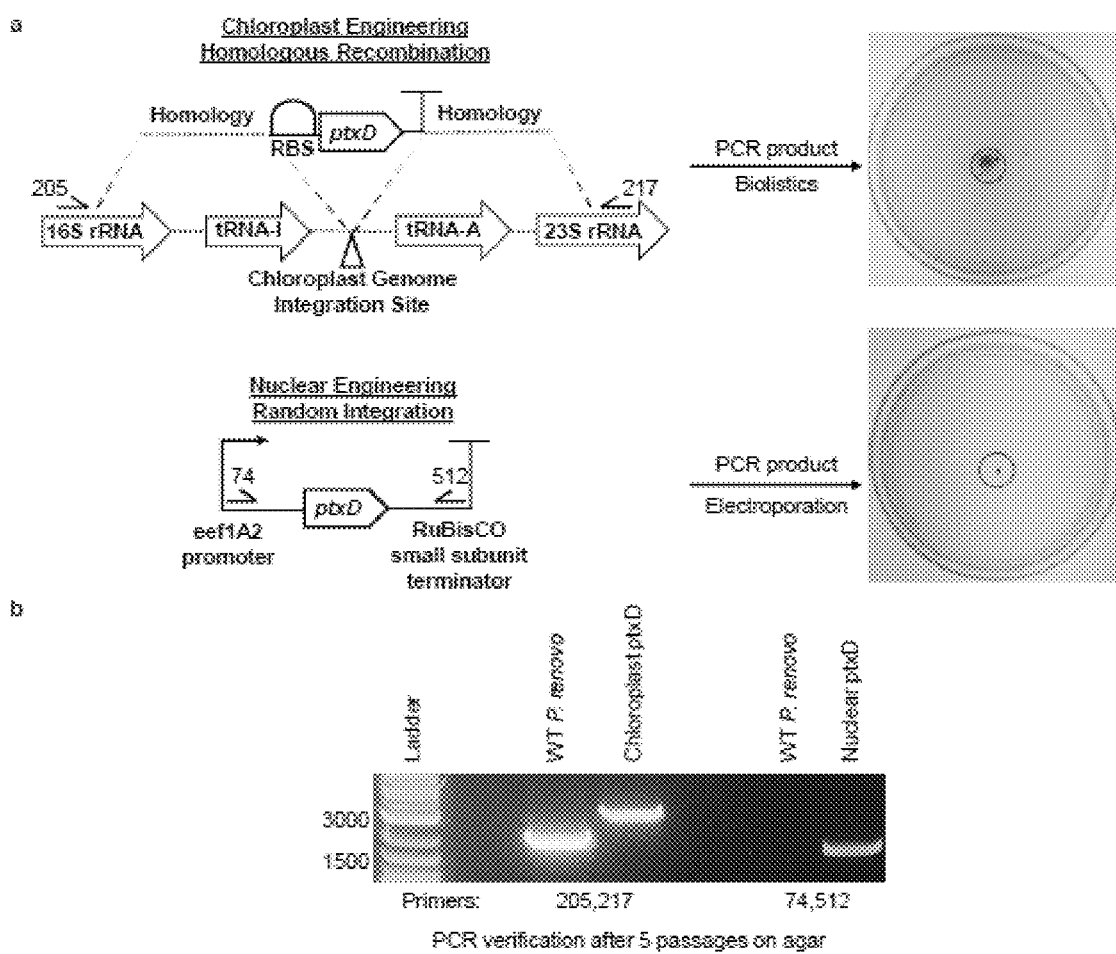
FIGS. 2A, 2B, depict an overview of ptxD expression in P. renovo.

Phosphite utilization in P. renovo was established through plastidial or nuclear expression of the ptxD gene from *Pseudomonas stutzeri* WM88. NADP+, as opposed to NAD+, is commonly considered the primary coenzyme in plant chloroplasts. However, the native *P. stutzeri* ptxD gene preferentially utilizes NAD+ as a cofactor. Leveraging work from prior reports, a mutated ptxD capable of NADP+ and NAD+ utilization was used for plastidial expression. This mutated ptxD gene (SEQ ID NO: 1) was codon optimized and integrated into the tRNA-I, tRNA-A locus of the chloroplast genome, using our previously reported methodology. SEQ ID NO: 2 is the amino acid sequence of the expressed mutated ptxD (SEQ ID NO: 1) capable of NADP+ and NAD+ utilization was used for plastidial expression. Chloroplast expression was facilitated by extending the native 16S rRNA operon, a computationally predicted ribosomal binding site (RBS), and a synthetic *E. coli* terminator (FIG. 2A). Positive transformants were readily obtained utilizing our previously established biolistic protocol. In contrast to our previous work, the native promoter element was removed such that transcription occurs via an upstream promoter element in the chloroplast genome. Additionally, the native terminator element was replaced with a synthetic terminator to remove homology to other elements native to the chloroplast genome (FIG. 2A). Combined, these changes, paired with the use of phosphite as a selectable marker, led to the obtainment of homoplasmy of the chloroplast genomes, as evident by the lack of a PCR band corresponding to the wild-type chloroplast genome (FIG. 2B). Homoplasmy and proper insertion was verified using the primers depicted in FIG. 2. Notably, colonies of P. renovo were apparent 5 days post particle bombardment, as compared to the ~21-30 days previously reported to obtain transgenic Chlamydomonas colonies.

To establish nuclear transformation capacity, the native *Pseudomonas stutzeri* ptxD enzyme was codon optimized for expression from the P. renovo nuclear genome and expressed under the control of a native P. renovo elongation factor promoter, as described previously (FIG. 2). SEQ ID NO: 3 is the nucleotide sequence of the native *Pseudomonas stutzeri* ptxD gene that is codon optimized for expression from the P. renovo nuclear genome. SEQ ID NO: 4 is the amino acid sequence of the expressed native *Pseudomonas stutzeri* ptxD gene that is codon optimized for expression from the P. renovo nuclear genome. Functional expression was achieved via the employ of a 150 base pair promoter, in contrast to our prior nuclear transformation work, wherein a promoter element of 650 base pairs was utilized, thereby simplifying future DNA cloning and synthesis endeavors. Nuclear transformation efficiency was markedly reduced by ~10 fold when selection occurs via phosphite, as compared to our previously established phleomycin (ble) gene selection marker, potentially due to differential mechanisms of action or residual phosphite toxicity.

Growth and Compositional Analyses

Figures 3A, 3B, 3C, 3D:
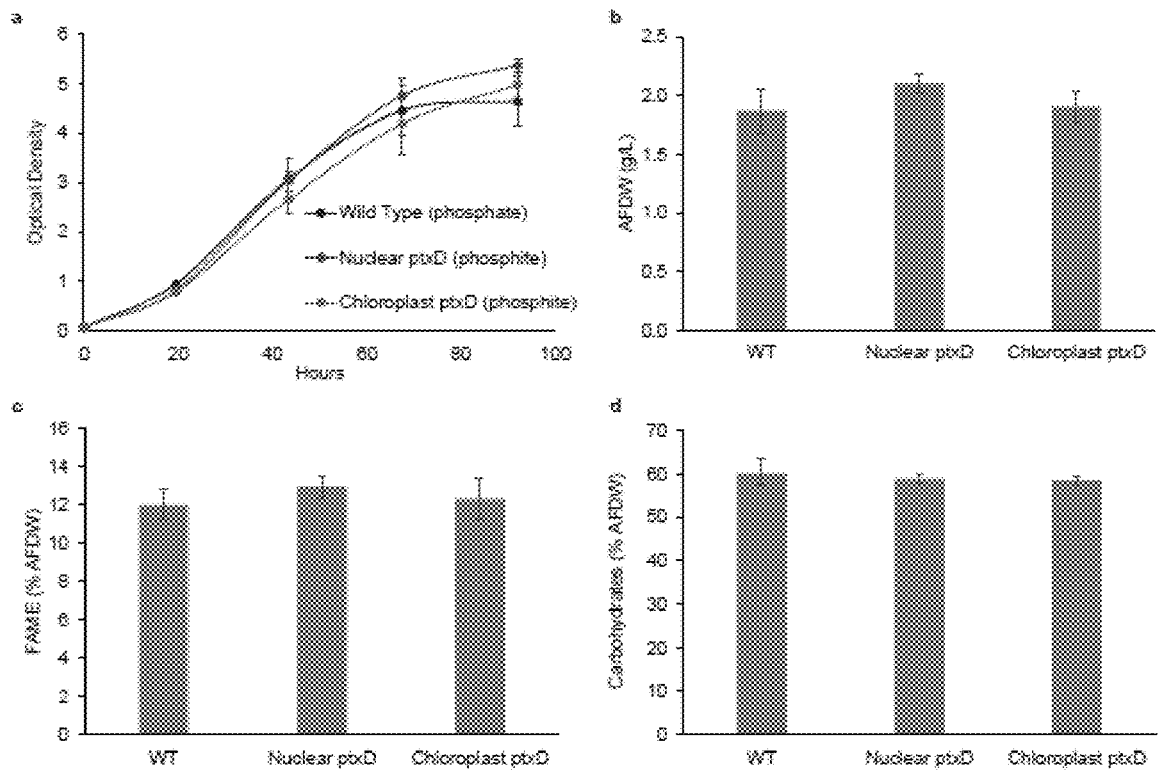
FIGS. 3A, 3B, 3C, and 3D depict growth and compositional analyses of P. renovo.

In order for phosphite to be effectively utilized in mass cultivation, growth on phosphite must cause minimal to no growth defects. We analyzed growth of these plastidial and nuclear transformants grown on phosphite compared to the wild-type strain grown on phosphate, to determine if any differential was evident. Growth of these transformants on phosphite was equivalent to that of the wild-type strain on phosphate, as measured by optical density curves and endpoint ash-free dry weight (AFDW, ~1.9 g/L) (FIGS. 3a, 3b). Compositional analysis of intracellular lipids and carbohydrates were also equivalent (~12% lipids, ~60% carbohydrates) (FIGS. 3c, 3d), in line with our previously reported stationary phase composition for this alga. Combined, these data show no growth or carbon partitioning differential for strains cultivated on phosphite as a sole phosphorus source.

Expression of Phosphite Dehydrogenase in Picochlorum Celeri

Picochlorum spp. are rapidly gaining interest in the algal community. Thus, we sought to evaluate transferability of phosphite-mediated selection across species of this genus. A query of the P. celeri genome indicated the nuclear elongation factor promoter and RuBisCO small subunit terminator utilized above in P. renovo had 99% homology (149/150 and 498/504 identical base pairs, respectively). As such, we hypothesized these P. renovo genetic elements would also be functional in P. celeri. Contrary to prior reports, our electroporation protocol for P. renovo readily obtained nuclear transformants in P. celeri.

Figures 5A, 5B:
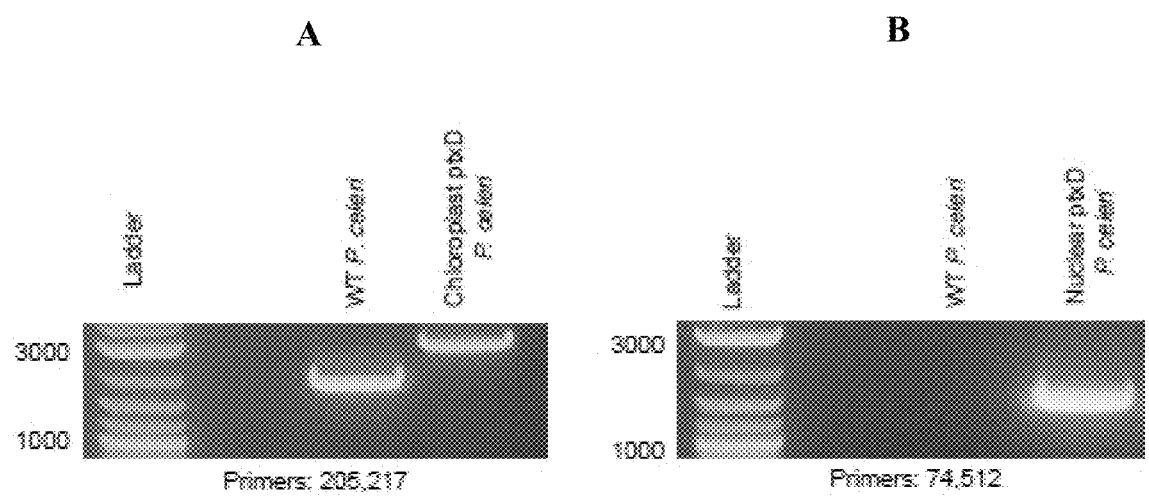
FIGS. 5A and 5B depict verification of P. celeri ptxD transformants via PCR and gel electrophoresis.

The above-described methodology for chloroplast transformation was also paralleled for P. celeri. However, as chloroplast integration occurs via homologous recombination and extension of the native 16S rRNA operon, we sought to decrease any complications with disrupting this operon and assembled a plasmid with P. celeri-specific homology arms for ptxD expression in the chloroplast. Our previously established biolistic protocol for P. renovo readily obtained the first reported plastidial transformants for P. celeri. Integration of transgenic DNA and homoplasmy was confirmed via PCR (FIG. 5).

Figures 6A, 6B, 6C, 6D:
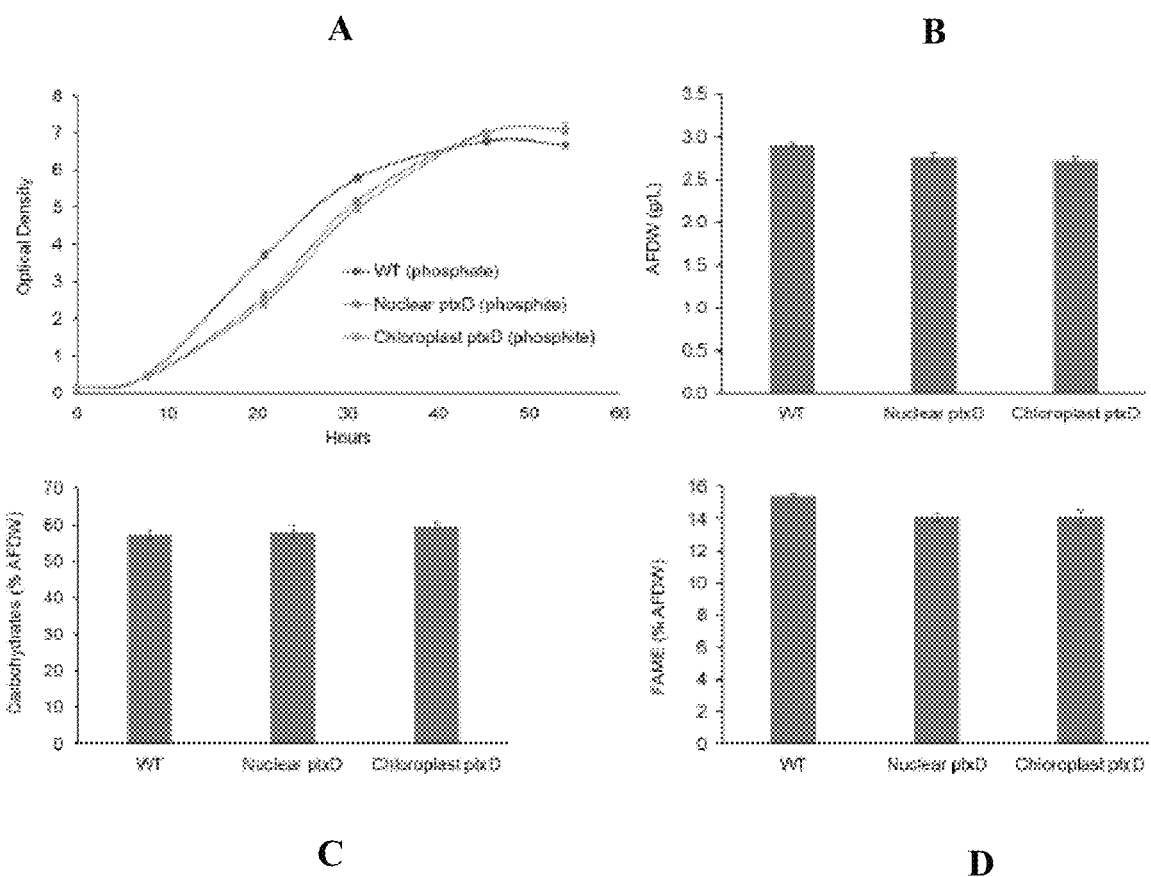
FIGS. 6A, 6B, 6C, 6D depict growth and compositional analyses of P. celeri.

We next compared growth of these P. celeri transformants to the wild-type strain; similar to the results obtained in P. renovo, there was minimal biomass accumulation differential between the wild-type strain grown on phosphate and transformants grown on phosphite (FIG. 6). P. celeri had a comparable composition to that of P. renovo for stationary phase cultures, reflective of relatively low lipid content (~13%) and high carbohydrate content (~57%).

Figure 4A:
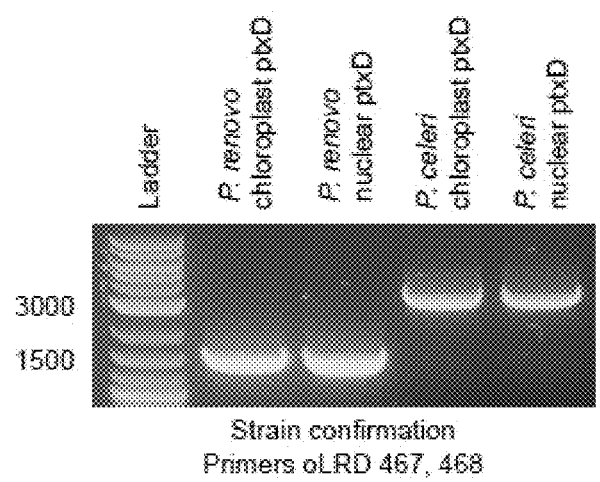
FIGS. 4A, and 4B depict a PCR test utilized to distinguish between P. renovo and P. celeri.
Figure 4B:
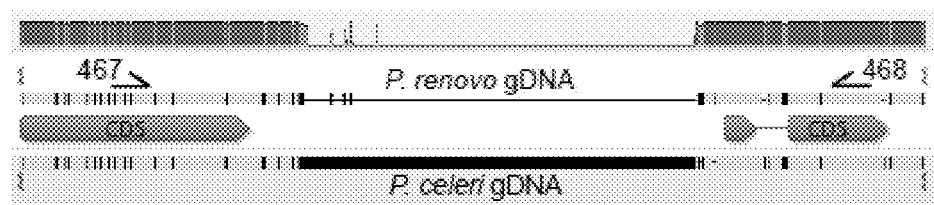

To confirm there was no cross contamination between these highly similar Picochlorum 75 species, we developed a facile PCR test to differentiate these strains. This methodology amplifies a section of nuclear genomic DNA wherein P. celeri possesses an additional ~1.5 kb of DNA in an otherwise homologous region between the two species. PCR primers flanking this region coupled with PCR and gel electrophoresis allows for a rapid distinction between strains (FIG. 4).

The work reported here expands the genetic toolbox available to the Picochlorum genus by establishing the use of phosphite as a selection agent in either the nucleus or chloroplast genomes and developing speciation probes. Importantly, phosphite mediated engineering also enabled the first report of chloroplast transformation in P. celeri. This strategy can also facilitate antibiotic-free genetic engineering and/or potential trait stacking in both the nucleus and chloroplast when utilized with previously established selectable markers. Notably, the employ of phosphite as a plastidial engineering tool enabled homoplasmy, which is critical for transgene stability and knockout strategies.

Phosphite-mediated cultivation led to equivalent biomass productivity and composition in two Picochlorum species. These data suggest phosphite presents a viable phosphorus source for outdoor cultivation of Picochlorum spp. Multi scale cultivation and competition experiments to assess the efficacy and economic viability of cultivation are contemplated with additional processes employing phosphite as a sole phosphorus or intermittent crop protection agent. Further, metagenomic analyses of non-sterile cultures lends insight into the presence of competing algae and predators capable of growth in phosphite containing media.

In addition to the crop protection benefits conferred by phosphite, this strategy also presents an opportunity for phosphite mediated biocontainment. Prior work in cyanobacteria has established such a system wherein ptxD and a phosphite-specific transporter (HtxBCDE) are co-expressed, while concurrently knocking out the native phosphate transporters. This strategy ensures containment of genetically modified organisms in the natural environment where phosphate is prevalent and phosphite is relatively limited. This, in turn, decreases the potential for gene flow from genetically modified organisms and propagation and/or disruption of native ecosystems, minimizing concern related to regulation of transgenic algae harboring this system.

Methods

Cultivation Conditions

Microalgae were cultivated under constant illumination at $\mu mol/m^2/s$ of light, 2% $CO_2$, and constant temperature of 33° C. These conditions were utilized to generate seed cultures for transformation and outgrowth of transformants to generate clonal isolates on agar plates. Media was comprised of a modified f/2 recipe, as described previously. For phosphorus source utilization analyses, agar plates were prepared as described previously, utilizing 8.75 g/L salinity, via dilution of seawater. Sodium phosphite dibasic pentahydrate (Sigma 04283) was utilized as a source of phosphite for this and subsequent experiments. Approximately 4.75× 108 early log phase cells were plated and incubated under the above conditions; plates were imaged after 5 days of growth.

To compare P. renovo transformants grown on phosphite to wild-type grown on phosphate, 50 mL of culture, inoculated from a mid-log culture at an optical density (750 nm) of 0.08 was grown in a 125 mL Erlenmeyer flask, and mixed via magnetic stirring. Media composition was as described above, except at a reduced salinity of 8.75 g/L, via dilution of the seawater. Cultures were grown at constant 280 $\mu mol/m^2/s$ of light and 1.5% $CO_2$ in a Percival cultivation chamber (Percival Scientific). Optical density growth curves were generated using a TECAN M plex microplate reader, equipped with cuvette reader functionality (Tecan Group Ltd).

To compare P. celeri transformants grown on phosphite to wild-type grown on phosphate, 50 mL of culture, inoculated from a mid-log culture at an optical density of 0.15 was grown in a 250 mL Erlenmeyer flask, mixed on a shaker platform (200 rpm). Media composition was as described above at a salinity of 35 g/L (seawater). These cultures were grown at constant 450 μmol/m²/s of light and 2% $CO_2$.

Construct Assembly and Transformation

The nuclear construct for ptxD expression was assembled via InFusion assembly (Takara Bio) of a pUC19 vector backbone and a synthesized gene fragment containing the P. renovo elongation factor promoter, ptxD gene from *Pseudomonas stutzeri* WM88, and P. renovo RuBisCO small subunit terminator (TWIST biosciences). Following assembly and sequence verification, a linearized PCR product of the ptxD gene and associated regulatory elements (Q5 Hot Start High-Fidelity 2X Master Mix, New England Biolabs, M0494L) was generated with primers oLRD74 and oLRD512 for transformation of P. renovo and P. celeri. Nuclear transformation was performed as described previously, with minor modification. Briefly, ~4.75×10⁸ early log phase cells were harvested, washed with 375 mM D-sorbitol and electroporated at 1900 volts and a 35 ms time constant with 4 μg of PCR linearized DNA.

The P. renovo chloroplast ptxD vector was assembled via InFusion assembly of our previously established vector (pLRD037, PCR linearized with oLRD245 and oLRD286) and a synthesized gene fragment of an RBS (ATTGATATTAAGCTCTTTCTAACG), mutated ptxD gene (to greatly increase NADP+ utilization), and a synthetic terminator. The assembled plasmid was sequence verified and a linearized PCR product comprised of the homology arms (to the tRNA-I and tRNA-A region), RBS, ptxD gene, and terminator was generated with Q5 polymerase and primers oLRD208 and oLRD209, for biolistic transformation of P. renovo.

The P. celeri chloroplast ptxD vector was assembled via InFusion assembly of homology arms (to the tRNA-I and tRNA-A region) amplified from P. celeri gDNA (Lucigen MasterPure Yeast DNA Purification Kit) and a PCR product containing the ribosomal binding site, ptxD gene and terminator was amplified with oLRD409 and oLRD253, utilizing the above P. renovo construct as a template. The upstream and downstream homology arms were PCR amplified with oLRD480 and oLRD481, and oLRD482 and oLRD483 respectively. This was assembled into a pUC19 backbone to yield an intact plasmid. A PCR product utilizing this new plasmid as a template was generated with primers oLRD496 and oLRD497 for transformation, containing the relevant homology arms, RBS, ptxD gene, and terminator.

Chloroplast transformation was performed. Briefly, DNA 268 (4.5 μL at 1000 ng/μL) was precipitated onto 550 nm gold microcarriers (30 μt, Seashell Technology, now Critter Technology), utilizing $CaCl_2$ (25 μL at 2.5 M) and spermidine (10 μl at 0.1 M). Cells were plated directly onto the above media at a salinity of 8.75 g/L, 271 with phosphite in place of phosphate for media formulation. These cells were bombarded with the DNA coated gold microcarriers utilizing a 1100 psi rupture disk at 25 in of Hg vacuum. Colony PCR, via boiling in Y-PER (ThermoFisher), and gel electrophoresis was performed as reported previously, to verify insertion.

Compositional Analysis

Compositional analysis for lipids, measured as fatty acid methyl esters (FAME), and carbohydrates, measured as monomeric sugars from hydrolyzed biomass was performed. Briefly, cells were harvested and following lyophilization were analyzed for residual moisture and ash to calculate ash free dry weight. FAME analysis was performed via trans-esterification of lyophilized biomass with chloroform and methanol, extracted with hexane and analyzed via gas chromatography and flame ionization detection. Carbohydrates were determined via hydrolysis of lyophilized biomass with sulfuric acid and autoclaving, analysis of the resultant monomeric sugars was performed via high pressure anion exchange liquid chromatography with pulsed amperometric detection.

Through the addition of the ptxD gene into the chloroplast genome of P. renovo the alga is able to utilize phosphite as a phosphorus source. Most organisms are not natively capable of utilizing phosphite, therefor this gene (ptxD) in combination with growth on phosphite is able to act as both a selectable marker, and as a way of reducing contamination in algal growth regimes.

In an embodiment, the methods and compositions disclosed herein can be used as a selectable marker for genetic engineering. In an embodiment, the methods and compositions disclosed herein can be used in methods to reduce contamination associated with cultivation of algae, particularly in outdoor environments.

In an embodiment, disclosed herein are methods and compositions that expand the suite of genetic tools and markers available for this genus (Picochlorum spp.), by heterologously expressing the phosphite dehydrogenase (ptxD) gene from *Pseudomonas stutzeri* WM88 in both the nucleus and chloroplast of Picochlorum renovo and Picochlorum celeri. The resultant strains allow for utilization of phosphite as a sole phosphorous source and as a nuclear and plastidial selection marker for genetic engineering. Growth analysis indicated comparable growth and composition when transgenic algae were grown in media containing phosphite as a sole phosphorus source, as compared to the conventionally used phosphate. Combined, these results expand the genetic toolbox available to the Picochlorum genus and present a potential crop protection and biocontainment strategy.

The foregoing disclosure has been set forth merely to illustrate the invention and is not intended to be limiting.

We claim:

1. A non-naturally occurring Picochlorum spp. capable of growth on phosphite as a sole phosphorus source wherein the Picochlorum spp. comprises a mutated ptxD gene with greater than 95% sequence identity to SEQ ID NO: 1.

2. The Picochlorum spp. of claim 1 comprising Picochlorum renovo.

3. The Picochlorum spp. of claim 1 comprising Picochlorum celeri.

4. The Picochlorum spp. of claim 1 comprising a mutated ptxD gene whose expressed enzyme has a sequence that is greater than 90% sequence identity to SEQ ID NO: 2.

5. The Picochlorum spp. of claim 1 wherein the mutated ptxD gene is expressed in the plastid.

6. The Picochlorum spp. of claim 4 wherein the expressed enzyme is capable of NADP+ and NAD+ utilization.

7. The Picochlorum spp. of claim 1 comprising a mutated ptxD gene with greater than 90% sequence identity to SEQ ID NO: 3.

8. The Picochlorum spp. of claim 7 comprising a mutated ptxD gene whose expressed enzyme has a sequence that is greater than 90% sequence identity to SEQ ID NO: 4.

9. The Picochlorum spp. of claim 7 wherein the mutated ptxD gene is expressed in the nucleus.

10. The Picochlorum spp. of claim 8 wherein the expressed enzyme is capable of NADP+ and NAD+ utilization.

11. A non-naturally occurring Picochlorum spp. capable of growth on phosphite as a sole phosphorus source comprising a mutated ptxD gene with greater than 95% sequence identity to SEQ ID NO: 1 and wherein the expressed enzyme from the mutated ptxD gene is capable of NADP+ and NAD+ utilization and wherein the non-naturally occurring Picochlorum spp. further comprises an exogenous phosphite-specific transporter.

12. The non-naturally occurring Picochlorum spp. of claim 11 wherein the exogenous phosphite-specific transporter is HtxBCDE.

13. The Picochlorum spp. of claim 11 comprising Picochlorum renovo.

14. The Picochlorum spp. of claim 11 comprising Picochlorum celeri.

15. The Picochlorum spp. of claim 11 wherein the mutated ptxD gene is expressed in the plastid.

16. A non-naturally occurring Picochlorum spp. capable of growth on phosphite as a sole phosphorus source comprising a mutated ptxD gene with greater than 90% sequence identity to SEQ ID NO: 3 and wherein the expressed enzyme from the mutated ptxD gene is capable of NADP+ and NAD+ utilization and wherein the non-naturally occurring Picochlorum spp. further comprises an exogenous phosphite-specific transporter.

17. The Picochlorum spp. of claim 16 comprising a mutated ptxD gene whose expressed enzyme has a sequence that is greater than 90% sequence identity to SEQ ID NO: 4.

18. The Picochlorum spp. of claim 16 wherein the mutated ptxD gene is expressed in the nucleus.

* * * * *